United States Patent [19]
Whitney

[11] Patent Number: 5,348,553
[45] Date of Patent: Sep. 20, 1994

[54] METHOD FOR PROMOTING BLOOD VESSEL HEALING

[76] Inventor: Douglass G. Whitney, 11200 Bowen Rd., Roswell, Ga. 30075

[21] Appl. No.: 809,334

[22] Filed: Dec. 18, 1991

[51] Int. Cl.⁵ .............................................. A61B 17/36
[52] U.S. Cl. ...................................... 606/41; 606/198
[58] Field of Search ................. 606/34, 198, 191, 192, 606/195, 194, 198, 41; 604/20, 21, 266; 128/784; 623/1

[56] References Cited

U.S. PATENT DOCUMENTS 4,733,665  3/1988  Palmaz .................................. 606/191
5,078,736  1/1992  Behl ........................................ 623/1
5,178,618  12/1993  Kandarpa ............................. 606/195

Primary Examiner—Lee S. Cohen
Assistant Examiner—Marianne Parker
Attorney, Agent, or Firm—B. J. Powell

[57] ABSTRACT

A method of repairing a blood vessel having a narrowed portion therein comprising the steps of expanding the narrowed portion of the blood vessel so that the diameter of the blood vessel after expansion is enlarged; and then maintaining an electronegative potential on the interior surface of the expanded narrowed portion of the blood vessel to at least as great as any electropositive potential generated by the blood vessel as a result of the injury to the blood vessel caused by the expansion thereof.

9 Claims, 2 Drawing Sheets

METHOD FOR PROMOTING BLOOD VESSEL HEALING

BACKGROUND OF THE INVENTION

This invention relates generally to cardiovascular repair and more particularly to a method and apparatus for promoting the healing of blood vessels following balloon angioplasty.

It is common practice to repair the narrowed segment of a diseased blood vessel by radially expanding the affected area of the blood vessel using a balloon catheter, commonly called balloon angioplasty. Early failure of such vascular repairs can occur shortly after the application of balloon angioplasty (commonly within the first 24 hours after application) typically due to blood clots or obstruction caused by the deformed plaque at the narrowed portion of the blood vessel. Late failure of such repairs can occur (usually about 3-6 months after application of therapy) due primarily to constriction of the passage through the blood vessel due to overgrowth of the smooth muscle portion of the blood vessel wall. The percentage of early failures is typically low while the percentage of late failures is relatively high (estimated at 40-70%).

More recently, attempts to overcome these problems have employed the use of stems that are placed in the blood vessels and left after the balloon angioplasty is performed. Examples of such techniques and equipment used to perform this repair are shown in the following patents:

| U.S. Pat. No. | Inventor | Issue Date |
| --- | --- | --- |
| 3,868,956 | Alfidi, et al. | 03/04/75 |
| 4,776,337 | Palmaz | 10/11/88 |
| 4,922,905 | Strecker | 05/08/90 |
| 4,969,458 | Wiktor | 11/13/90 |
| 5,019,090 | Pinchuk | 05/28/91 |

Experience has shown, however, that the stents have not been successful in overcoming the failures associated with balloon angioplasty. As a matter of fact, the stents have tended to fail more frequently than balloon angioplasty without the stents.

There have also been attempts to reduce blood clotting by using certain materials or circuits that generate an electronegative charge on the surface of artificial blood vessels used to surgically replace sections of the patient's vascular system or on the surface of receptacles to store blood. Examples of such techniques are illustrated in the following patents:

| U.S. Pat. No. | Inventor | Issue Date |
| --- | --- | --- |
| 3,512,183 | Sharp, et al. | 05/19/70 |
| 3,723,754 | Murayama, et al. | 03/27/73 |
| 3,726,762 | Puharich, et al. | 04/10/73 |

This technology has not been applied to nonsurgical balloon angioplasty in which the original blood vessel is not removed. As a matter of fact, prior art U.S. Pat. No. 3,512,183 suggests that this technology is not applicable to living tissue in the blood vessel.

SUMMARY OF THE INVENTION

These and other problems and disadvantages associated with the prior art are overcome by the invention disclosed herein by providing a technique for reducing, both early and late failures associated with balloon angioplasty. The invention helps prevent the attraction of platlets in the blood stream to the site of the enlarged narrowed portion of the blood vessel and helps regenerate the intima layer on the inside of the repaired area of the blood vessel. As a result, the early failures of the prior art techniques associated with blood clotting are reduced since the extent of blood clotting is significantly reduced. Also, late failures of the repaired blood vessel are greatly reduced since the level of growth chemicals released by the platelets attracted to the site is reduced thereby diminishing the overgrowth of the vessel wall normally associated with the healing process after the use of prior art techniques. The technique of the invention also includes transferring intima cells to the site on the stent so that regeneration of the intima layer along the inside of the repaired site is facilitated.

The method of the invention includes nonelastically expanding the narrowed portion of the blood vessel and then maintaining an electronegative potential on the interior surface of the expanded narrowed portion of the blood vessel to at least offset any electropositive potential generated by the current of injury in the blood vessel following balloon angioplasty. The expansion of the blood vessel may be accomplished with a balloon catheter and a stent may be installed to act not only as a mechanical brace to keep the artery open but also as a conductor on which the electronegative potential is imposed. An electronegative charge is maintained through the stent on the interior surface of the blood vessel which is sufficient to prevent the platlets from adhering to the vessel wall. The surface intimal cells may be applied to the repaired blood vessel by wiping them from the lining of a non-vital blood vessel onto the stent prior to being installed, so that, once the stent has been ballooned into place, these intimal cells serve as a source for rejuvenating the intima.

These and other features and advantages of the invention will become more clearly understood upon consideration of the following detailed description and accompanying drawings wherein like characters of reference designate corresponding parts throughout the several views and in which:

These FIGURES and the following detailed description disclose specific embodiments of the invention, however, it is to be understood that the inventive concept is not limited thereto since it may be embodied in other forms.

DETAILED DESCRIPTION OF ILLUSTRATIVE EMBODIMENTS

Figure 1:
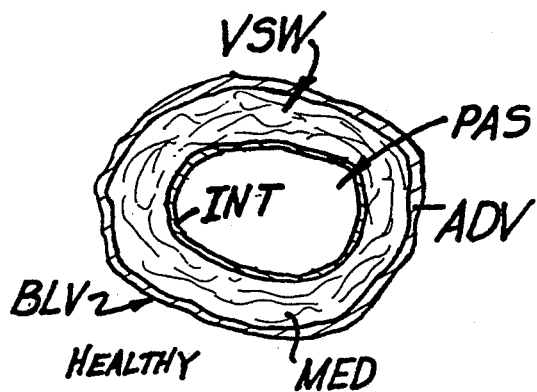
FIG. 1 is an enlarged cross-sectional view of a healthy blood vessel.

The vessel wall VSW of a normal artery or other blood vessel BLV has several portions when seen in cross-section. There is an outer layer or adventicia ADV on its exterior surface, a central portion or media MED, and a surface lining of cells or intima ITM on its luminal or interior surface. As schematically illustrated in FIG. 1, the interior and exterior surfaces INT and EXT of the blood vessel BLV are oppositely charged with an electronegative charge on the interior surface INT and an electropositive charge on the exterior surface EXT. Thus, the negative charge on the interior surface INT serves to repel the negatively charged blood passing through the blood vessel and maintain free passage of the blood. In the event of an injury to the vessel wall, these charges reverse so that the negatively charged platelets in the blood stream are attracted to the interior surface INT to start the blood clotting and injury healing process. This reversal of charge is called a current of injury. This electropositive current of injury is responsible, to a great extent, for the normal response of the body to control hemorrhage or bleeding from an injured vessel wall.

Figure 2:
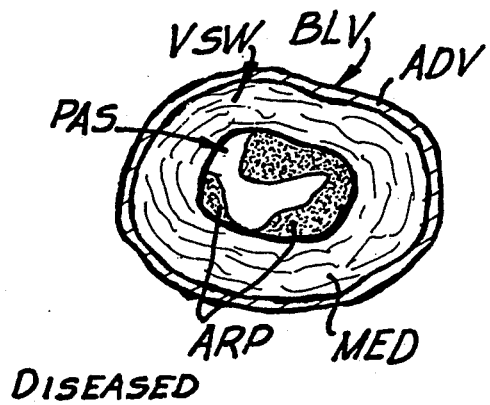
FIG. 2 is an enlarged cross-sectional view of a diseased blood vessel.

Whereas a normal artery or other blood vessel has an intimal cell lining on its luminal or interior surface, a diseased artery is frequently denuded of this intimal lining and has a raw surface of arteriosclerotic plaque ARP as seen in FIG. 2. The normal electronegative surface potential of the healthy intimal lining may not be present. The process of balloon angioplasty, in fact, injures an artery or vessel wall and sets the stage for recurrence of injury which can, in fact, be responsible for failure of the balloon angioplasty.

Figure 3:
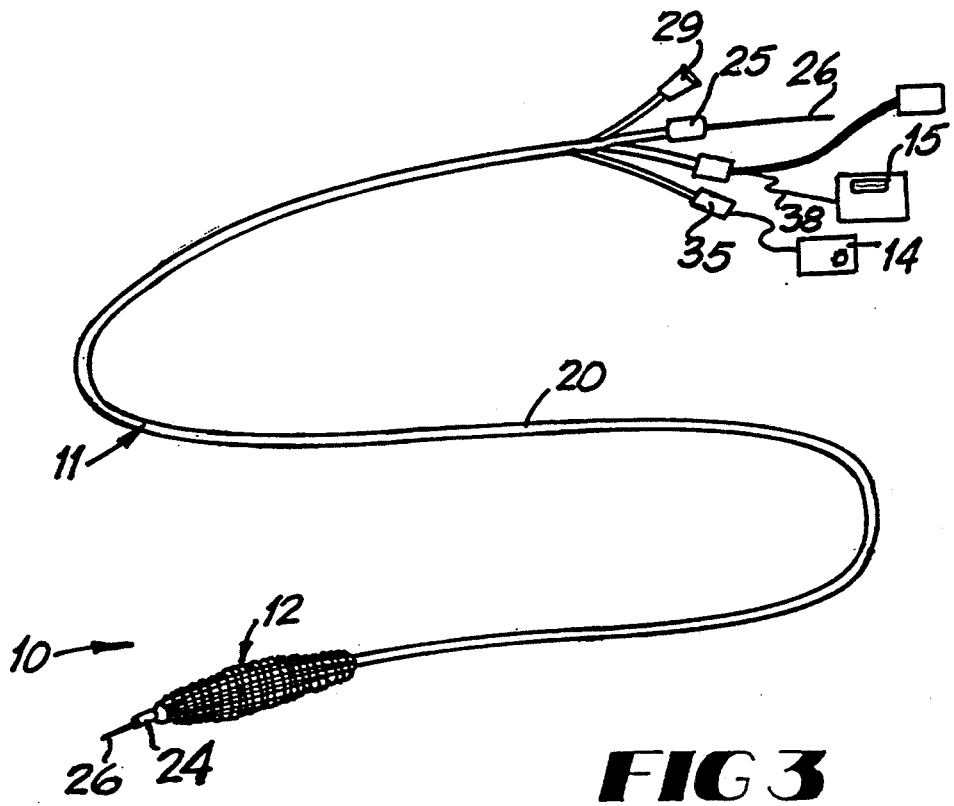
FIG. 3 is a view illustrating the system of the invention.
Figure 4:
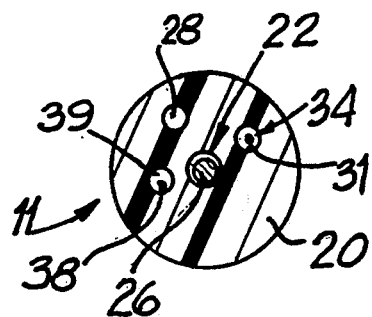
FIG. 4 is a transverse cross-sectional view of the catheter of the invention.

Referring to FIG. 3, the apparatus of the invention is a system 10 which includes a balloon catheter 11 on which is carried an electrically conductive stent 12. The conductive stent 12 is connected to a power supply 14 that is located externally of the patient to maintain an electronegative potential on the stent 12 after it is installed in the blood vessel. An electrical measuring apparatus 15 may also be used with the catheter 11 to adjust the charge on the stent 12 after it is in place in the blood vessel.

The catheter 11 corresponds generally to balloon catheters used for balloon angioplasty and includes a multi-lumen elongate thin main body 20 on the leading end of which is mounted an inflatable balloon 21. The body 20 defines a guide wire lumen 22 therethrough from its leading end 24 to the wire inserting fitting 25 at its opposite end to fit over the guide wire 26 normally associated with the insertion of the catheter 11 into the patient's blood vessel. The body 20 also defines a pressure lumen 28 therein which communicates with the balloon 21 on the leading end of the catheter and opens through the pressure fitting 29 at the opposite end of the body 20 as is typical with balloon catheters.

The stent 12 may have any of a wide variety of constructions as long as the stent is capable of carrying the electronegative potential within the range required to offset the current of injury in the blood vessel and is also capable of being located on the interior surface INT of the patient's blood vessel. Preferably, the stent 12 is capable of being nonelastically expanded from a diameter smaller than the free passage through that portion of the blood vessel which has been narrowed to the accumulated arteriosclerotic plaque. The stent 12 illustrated in FIG. 7 has an open plastic or metal wire mesh construction which is electrically conductive. Any of a wide variety of materials may be used without departing from the scope of the invention. Preferably, the metal wire mesh is in an annealed condition so that the stent can be expanded by the balloon 21 into contact with and supports the blood vessel wall and will have limited recovery to remain in contact with the vessel wall after the balloon 21 has been deflated.

Figure 7:
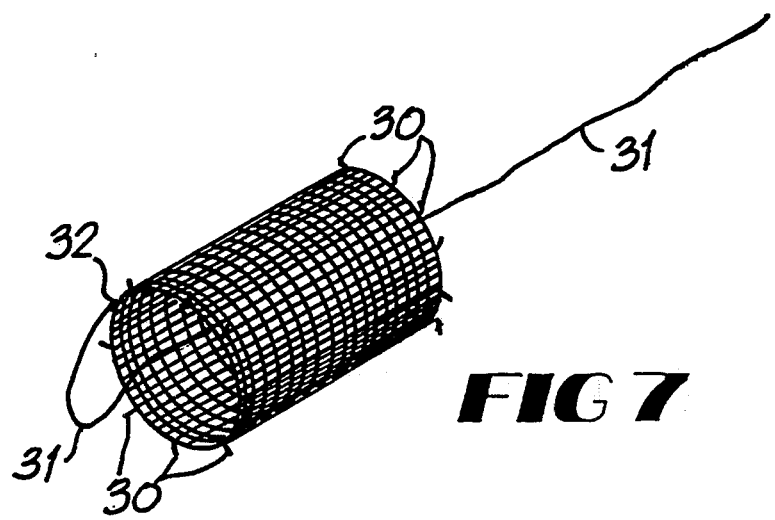

After the stent 12 is expanded into position in the blood vessel, it must remain in that position. As seen in FIG. 7, outwardly projecting prongs 30 may be provided on opposite ends of the stent 12 that engage the blood vessel wall to keep the stent in place. To supply a voltage to the stent 12 from the power supply 14, a supply wire 31 extends from one end of the stent 12 and passes out through the opening in the blood vessel through which the catheter passes. The wire 31 is appropriately insulated along its length to prevent the flow of current between the wire and the other sections of the blood vessel. The end of the wire 31 projecting out of the patient's body is connected to the voltage source 14 so that the appropriate electronegative voltage is imposed on the stent 12 and thus the interior surface INT of the blood vessel at the location of the stent. The wire 31 is connected to the end of the stent 12 through a break away section 32 best seen in FIG. 7. To accommodate the wire 31 while the stent 12 is being installed, stent lumen 34 is provided through the catheter body 20 that opens onto the leading end 24 of the body. The stent 12 is preliminarily placed over the end of the catheter and onto the balloon 21 with the wire 31 passing through the lumen 34 and out of the fitting 35 on the catheter 11 so that it can be connected to the power supply 14 even while the catheter is in position in the blood vessel. This allows the electronegative potential to be imposed on the stent 12 while the catheter is still in place in the blood vessel. To remove the catheter after the stent 12 has been placed without pulling the wire 31 off the stent, the wire 31 is disconnected from the power supply 14 and allowed to slide in the lumen 34 as the catheter body is removed. This leaves the wire 31 in the blood vessel and projecting out of the opening through which the catheter 11 was inserted. The power supply 14 can then be reattached to the wire 31 and the power level left at the setting to which it was adjusted when the catheter was still in position in the blood vessel. Once the need for the electronegative potential is over, the wire 31 can be easily removed while leaving the stent 12 in place by simply pulling on the wire 31 outside the patient to break the wire free at the break away section 32.

Alternatively, the necessary electronegative potential may be provided by the patient's own body. The end of the wire 31 opposite the stent 12 may be connected to a capacitive blocking device such as a capacitor and the opposite side of the capacitive blocking device electrically connected to another part of the patient's body capable of generating a current of injury. Typical of such body parts would be a healthy artery or a healthy muscle. The body part would be injured sufficiently after the wire to the capacitive blocking device was installed to cause the body part to generate the electropositive potential associated with such injury to the blocking device which in turn will generate the electronegative potential on the opposite side of the capacitive blocking device connected to the wire 31 so that the generated electronegative potential will be imposed on the stent 12. The real advantage to this arrangement is that the electronegative potential at the stent 12 will be readjusted at the healing rate of the injured body generating the electropositive potential so that the electronegative potential on the stent 12 is reduced at the normal healing rate of the patient.

To monitor the electronegative potential at the stent 12 after it is installed, a silver sensing wire 38 that has been treated in a silver, silver chloride solution so as to detect the net potential at the inside surface of the blood vessel is provided that extends in a detection lumen 39 in the body 20 to a position adjacent the leading end 24 of the catheter 11. A small communication opening is provided to the lumen 39 so that the saline solution can communicate with the interior of the blood vessel to establish electrical communication with the interior surface INT of the blood vessel at the position at which the stent 12 is installed. The electrical measuring apparatus 15 is connected to the sensing wire 38 exteriorly of the patient to measure the electronegative potential at the stent 12. The output of the power supply 14 is adjusted to return the electronegative potential at the stent site back to the potential it had before the balloon angioplasty to allow the intima layer ITM to regenerate.

To provide intima cells at the stent site, the catheter 11 with the unexpanded stent 12 thereon is inserted in a healthy section of the blood vessel BLV and the stent 12 rubbed against the healthy intima layer INT so that some of the intima cells are caught in the stent 12. The catheter 11 is then moved to the site to have the balloon angioplasty applied. The intima cells remain caught in the stent 12 after it is installed to serve as a starter for the regenerated intima layer at the repaired site.

Figure 5:
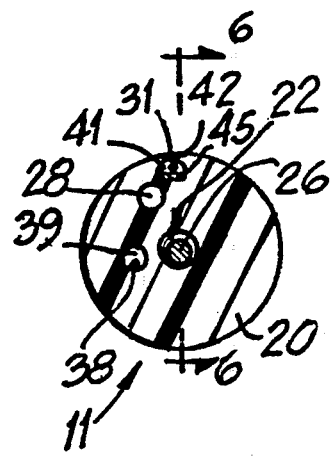
FIG. 5 is a transverse cross-sectional view of a second embodiment of the catheter of the invention.
Figure 6:
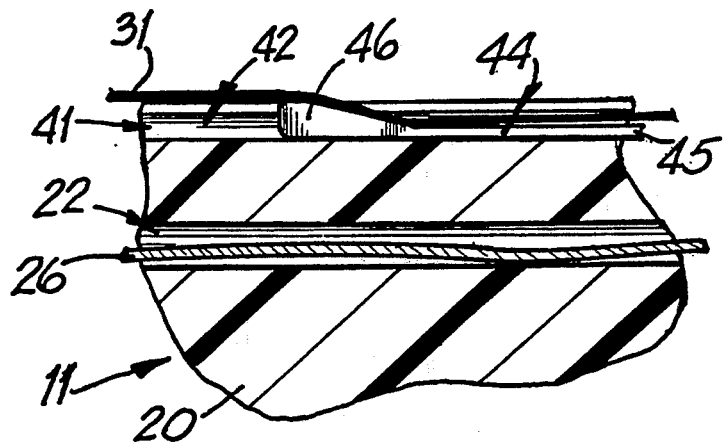
FIG. 6 is a longitudinal cross-sectional view of the second embodiment of the catheter of the invention taken generally along line 6—6 in FIG. 5; and, FIG. 7 is an enlarged perspective view of the stent used in the invention.

An alternative arrangement for removably mounting the charged supply wire 31 in the body 20 is illustrated in FIGS. 5 and 6. The wire 31 is recessed in a channel 41 provided with an access slit 42 to the exterior surface of the body 20 and extends along the length thereof so that the wire 31 can be displaced from the channel 41 through the access slit 42. To displace the wire 31 from the channel 41 while the catheter 11 is in place in the blood vessel BLV, a displacing member 44 is provided in the bottom of the channel 41 with an activating portion 45 that extends along the length of the catheter body 20 and a displacing section 46 on the projecting end thereof that projects out of the channel 41 through the access slit 42. When that end of the activating portion 45 extending out of the catheter 11 exteriorly of the patient is pulled, the displacing section 46 moves along the length of the channel 41 and displaces the wire 31 out of the channel. After the wire 31 is displaced out of the channel, the catheter 12 can be removed in the usual manner.

What is claimed as invention is:

1. A method of repairing a blood vessel having a narrowed portion therein comprising the steps of:
   (a) expanding the narrowed portion of the blood vessel so that the diameter of the blood vessel after expansion is enlarged;
   (b) maintaining an electronegative potential on the interior surface of the expanded narrowed portion of the blood vessel to at least as great as any electropositive potential generated by the blood vessel as a result of an injury to the blood vessel caused by the expansion thereof.

2. The method of claim 1 wherein step (a) comprises the substeps of:
   (a1) inserting a balloon catheter into the narrowed portion of the blood vessel until a collapsed balloon on the catheter is in alignment with the narrowed portion of the blood vessel; and
   (a2) inflating the balloon to forcibly enlarge the narrowed portion of the blood vessel.

3. The method of claim 1 further comprising the step of:
   (c) locating a stent in the expanded narrowed portion of the blood vessel with the stent in contact with the interior surface of the expanded narrowed portion of the blood vessel; and maintaining the electronegative potential on the stent to at least offset said electropositive potential.

4. The method of claim 1 further comprising the step of:
   (c) locating intimal cells on the interior of the expanded narrowed portion of the blood vessel to promote the formation of surface lining of intimal cells on the interior surface while the electronegative potential is maintained thereon.

5. The method of claim 1 further comprising the steps of:
   (c) locating an electrically conductive stent in the expanded narrowed portion of the blood vessel with the stent in contact with the interior surface of the expanded narrowed portion of the blood vessel; and maintaining the electronegative potential on the stent to at least offset said electropositive potential; and
   (d) locating intimal cells on the interior of the expanded narrowed portion of the blood vessel to promote the formation of surface lining of intimal cells on the interior surface while the electronegative potential is maintained thereon.

6. The method of claim 1 wherein step (a) comprises the substeps of:
   (a1) locating a stent over a collapsed balloon of a balloon catheter where the stent has an initial diameter smaller than the narrowed portion of the blood vessel;
   (a2) inserting the balloon catheter into the narrowed portion of the blood vessel until the collapsed balloon on the catheter is in registration with the narrowed portion of the blood vessel while holding the stent in position over the collapsed balloon of the catheter; and
   (a2) inflating the balloon to forcibly enlarge the narrowed portion of the blood vessel and enlarge the stent into contact with the interior of the expanded narrowed portion of the blood vessel to help maintain the blood vessel enlarged; and
   wherein step (b) further includes the substep of
   (b1) maintaining the electronegative potential on the stent.

7. The method of claim 1 wherein step (b) further comprises maintaining a current density of about 50 milliamps per square centimeter on the interior surface of the blood vessel.

8. A method of repairing a blood vessel having a narrowed portion therein comprising the steps of:
   (a) detecting an electrical potential on the interior surface of the narrowed portion of the blood vessel;
   (a) expanding the narrowed portion of the blood vessel so that the diameter of the blood vessel after expansion is enlarged; and
   (c) applying an electronegative potential to the interior surface of the expanded narrowed portion of the blood vessel until the electrical potential on the interior surface is about equal to the detected electrical potential on the interior of the narrowed portion of the blood vessel to at least as great as any electropositive potential generated by the blood vessel as a result of an injury to the blood vessel caused by the expansion thereof.

9. The method of claim 8 wherein step (c) further comprises maintaining a current density of about 50 milliamps per square centimeter on the interior surface of the blood vessel.

* * * * *